United States Patent [19]
Langkilde

[11] Patent Number: 5,999,253
[45] Date of Patent: Dec. 7, 1999

[54] APPARATUS AND METHOD FOR SPECTROMETRY

[75] Inventor: Frans Langkilde, Holte, Denmark

[73] Assignee: Astra Aktiebolag, Sodertalje, Sweden

[21] Appl. No.: 08/776,169

[22] PCT Filed: Dec. 11, 1996

[86] PCT No.: PCT/SE96/01637

§ 371 Date: Jan. 22, 1997

§ 102(e) Date: Jan. 22, 1997

[87] PCT Pub. No.: WO97/22872

PCT Pub. Date: Jun. 26, 1997

[30] Foreign Application Priority Data

Dec. 20, 1995 [SE] Sweden .................................. 9504567

[51] Int. Cl.⁶ .............................. G01N 21/01; G01N 1/10; G01T 1/00
[52] U.S. Cl. .......................... 356/244; 356/246; 250/328; 250/341.1
[58] Field of Search .................................... 356/301, 346, 356/45, 246, 318, 244

[56] References Cited

U.S. PATENT DOCUMENTS

| | | | |
|---|---|---|---|
| 4,882,493 | 11/1989 | Ladder et al. | 250/353 |
| 5,568,253 | 10/1996 | Chan et al. | 356/246 |
| 5,627,645 | 5/1997 | Imagawa et al. | 356/364 |
| 5,638,171 | 6/1997 | Honig et al. | 356/246 |
| 5,774,209 | 6/1998 | Shestock | 356/73 |

FOREIGN PATENT DOCUMENTS

| | | |
|---|---|---|
| 0172663 | 2/1986 | European Pat. Off. . |
| 0634647 | 7/1994 | European Pat. Off. . |
| 4124278 | 1/1993 | Germany . |

*Primary Examiner*—Frank G. Font
*Assistant Examiner*—Roy M. Punnoose
*Attorney, Agent, or Firm*—White & Case LLP

[57] ABSTRACT

A device and a method are intended for use in a spectroscopic analysis, especially performed with the aid of Raman spectroscopy, of a solid sample, such as a tablet (1). By means of a sample holder (7), the sample (1) is positioned in relation to an excitation beam which, during implementation of the analysis, falls upon a reception surface of the sample (1), the impingement area (S) being smaller than the reception surface of the sample (1). The sample holder (7) is rotated about an axis of rotation (A) parallel to the excitation beam, such that the point of impingement (S) of the excitation beam describes an annular scanning trace (20) on the reception surface of the sample (1). During implementation of the analysis, the radius of the annular scanning trace (20) is varied to enable a fairly large volume of the sample to be analysed.

12 Claims, 4 Drawing Sheets

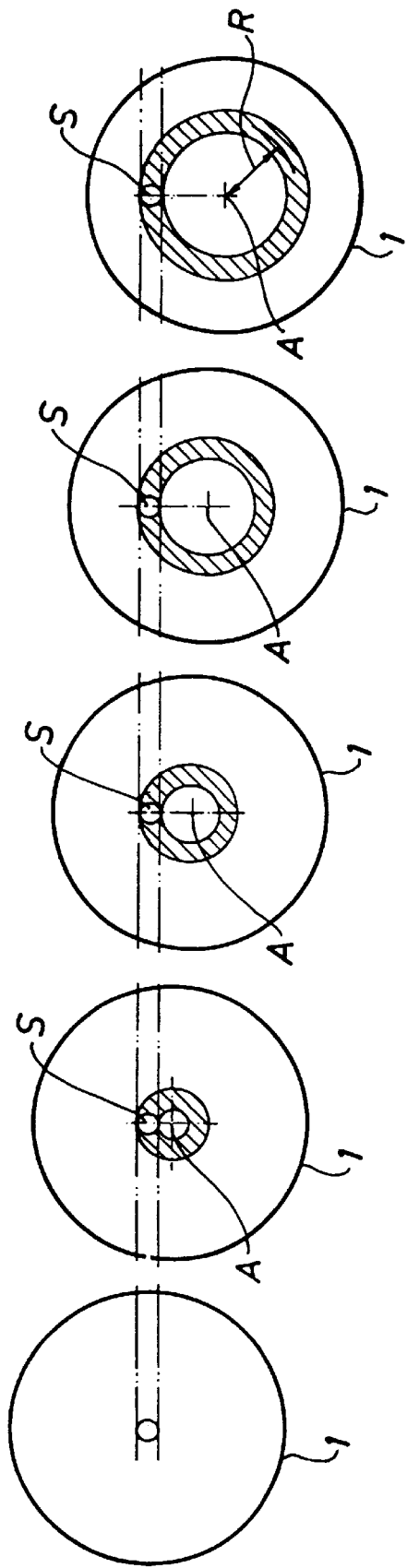

APPARATUS AND METHOD FOR SPECTROMETRY

FIELD OF THE INVENTION

This invention relates to the field of spectrometry and more specifically concerns a method and a device for use in the analysis of a solid sample, especially with the aid of Raman spectrometry.

BACKGROUND OF THE INVENTION

When analysing medicinal products with the aid of vibration spectrometry, one has resorted primarily to infrared (IR) spectrometry, since IR spectra provide detailed information on the molecular structure. Today's vibration spectrometry is divided into the following three main areas:

1. the middle part of the IR range;
2. the upper part (NIR) of the IR range; and
3. Raman spectrometry.

Obtaining and evaluating Raman spectra was previously, beginning in the year 1928 when the Raman effect was discovered, a fairly time-consuming and difficult procedure. The development of modern CCD units, advanced lasers and not least powerful hardware and software for data processing has, however, resulted in a considerable increase in the number of applications of Raman-based analysis. The advent of the FT technique (Fourier transform) for analysing signals obtained through Raman spectrometry constituted a breakthrough of particular importance. This technique enabled excitation in the NIR range (Near Infrared) resulting in a sufficiently powerful Raman signal without any interfering fluorescence. The FT-Raman technique is today used commercially for qualitative as well as quantitative analysis within a great many different fields, such as the analysis of polymers, hot gases (flames), medicinal products and biomaterial.

Being well-known to those skilled in the art, the Raman effect need not be described in more detail here. However, when an excitation beam (in practice a laser beam) is directed towards a sample (gaseous, liquid or solid) that is to be analysed, part of the incoming excitation beam is scattered in all directions at another wavelength (shorter or longer) from molecules whose polarization is altered when they are caused to vibrate by the field generated by the excitation beam. By intercepting the retransmitted radiation, one obtains a Raman spectrum upon which a quantitative as well as a qualitative chemical analysis can be based. When solid samples are measured, use is normally made of so-called back-scattering geometry, which means that the analysis involves the light that is reflected at an angle of 180° to the direction of incidence of the excitation beam.

When Raman spectrometry is applied to solid samples, one obtains a fairly large depth of penetration into the sample, for instance in the order of 1 mm. Bearing this in mind, one realises the potential of the Raman technique for e.g. the analysis of the ingredients, especially the active substances, of whole tablets.

In the analysis of solid samples, Raman spectrometry does, however, suffer from an inconvenience not encountered in NIR spectrometry, namely that the excitation beam (in practice a laser beam), has to have a very narrow focus. As a result, it is only possible to analyse a relatively small part of the total volume of the sample. If the sample, for instance a tablet, is homogeneous, there are no problems. If, however, the sample is inhomogeneous, as is often the case for tablets, the results of the analysis are not representative of the whole tablet, for instance as regards the concentration of an active substance.

In an illustrative example of Raman analysis of a tablet, the "part volume" of the total volume of the sample actually analysed by the beam may be in the form of a cone converging in the direction of the excitation beam and having a height of approximately 1 mm and a base diameter of approximately 0.4 mm at the impingement surface on the sample. For a typical tablet having a diameter of 10 mm and a thickness of 4 mm, the conical part volume analysed thus constitutes but a small part of the total volume of the tablet. This problem is not encountered in NIR spectrometry, where the excitation beam can be made to cover the entire irradiated surface of the sample.

This invention has been developed in an effort to solve, or at least substantially reduce, the above-mentioned problems from which suffer the prior-art technique in Raman spectrometry involving solid samples.

By the expression "solid samples" is here meant samples in which the analysed substance in itself is a solid unit, such as a tablet, samples where the substance to be analysed consists of a more or less compacted powder, or some other solid object placed in a sample container.

SUMMARY OF THE INVENTION

One aspect of the invention provides a device which is intended for use in a spectroscopic analysis of a solid sample, such as a tablet, and which comprises a sample holder for positioning the sample in relation to an excitation beam which, during implementation of the analysis, falls upon a reception surface of the sample, the impingement area being smaller than the reception surface of the sample. This device is characterised in that it comprises a drive means for causing the sample holder to rotate about an axis of rotation parallel to the excitation beam, such that the point of impingement of the excitation beam describes an annular scanning trace on the reception surface of the sample, and that it is adapted to vary the radius of the annular scanning trace during implementation of the analysis. As a result, a much larger surface will be scanned, and a much greater volume of the sample will thus be analysed than is the case when use is made of prior-art techniques.

In a first embodiment of the inventive device for performing a spectroscopic analysis of a solid sample having a circular peripheral surface, the axis of rotation of the holder is non-vertical, preferably horizontal, and the sample holder comprises a sample compartment defined by a cylinder surface which is concentric with the axis of rotation and rotates about it and whose diameter exceeds that of the circular peripheral surface of the sample, the sample being freely movable in the sample compartment and having its symmetry axis directed in parallel with the axis of rotation of the holder so as to roll against the cylinder surface when this rotates.

In this first embodiment, the rotation of the holder will not only cause the sample to rotate about its own symmetry axis as a result of the sample rolling against the cylinder surface of the holder at its peripheral surface, but also cause a reciprocating lateral displacement of the point of contact between the circular peripheral surface of the sample and the cylinder surface in relation to a vertical line coinciding with the axis of rotation of the holder. Owing to this combined movement, the distance between the point of impingement of the excitation beam and the symmetry line of the sample, i.e. the radius of the scanning trace, will vary.

In a preferred variant of the first embodiment of the inventive device, the sample compartment is so dimensioned that the sample placed therein is essentially fixed in relation to the holder in the direction of the axis of rotation but is freely movable in relation to the holder perpendicularly to the axis of rotation. This variant ensures that the excitation beam can be correctly focused on the sample during the whole analysis, while the sample is allowed to perform the above, combined movement of rotation and displacement.

A second embodiment of the inventive device comprises means which are arranged to parallel-displace the axis of rotation of the holder in relation to the excitation beam, thereby the achieve the variation of the radius of the scanning trace. This second embodiment of the inventive device may be used also for samples having a noncircular peripheral surface.

In the second embodiment of the inventive device, the holder is preferably adapted to keep the sample fixed in all directions in relation to the holder during implementation of the analysis.

Further, the first and the second embodiment of the device according to the invention may be combined.

A second aspect of the invention provides a method which has the distinctive features recited in appended claim 6 and which is intended for use in a spectroscopic analysis of a solid sample in accordance with the principles indicated above in connection with the inventive device. Preferred modes of implementation of the method are indicated in appended subclaims 7–12.

BRIEF DESCRIPTION OF THE DRAWINGS

Two embodiments of the invention will now be described in more detail with reference to the accompanying drawings, in which

FIGS. 8A–E schematically illustrate the function of the second embodiment of the device according to the invention.

DESCRIPTION OF THE PREFERRED EMBODIMENTS

Figure 1:
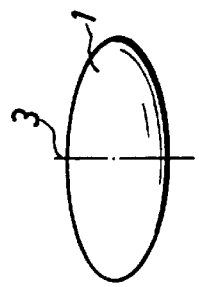
FIG. 1 is a side view of a tablet, the symmetry line of which is indicated.
Figure 4A:
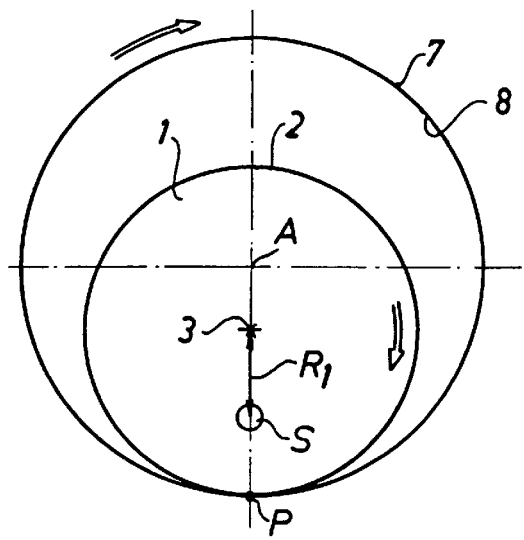
FIGS. 4–7 schematically illustrate the function of the first inventive embodiment shown in FIGS. 2 and 3.
Figure 5A:
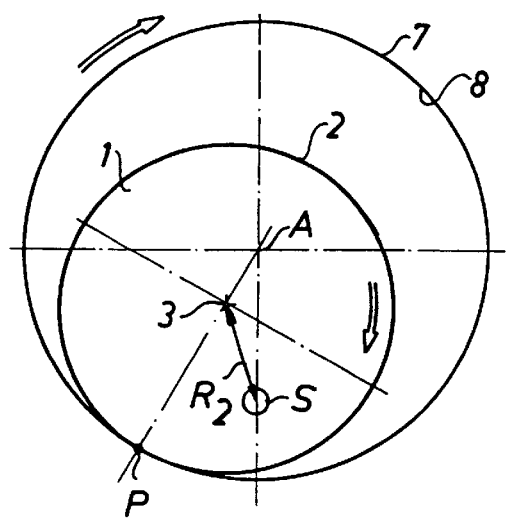

As an illustrative example of a solid sample intended to be analysed in accordance with the principles of the invention, FIG. 1 shows a tablet 1, such as a medicinal tablet, whose content is to be analysed with the aid of Raman spectrometry. This tablet typically has a diameter of about 10 mm and a thickness of about 4 mm, and its circular peripheral surface 2 (FIGS. 4–6) has a symmetry line 3 indicated in FIG. 1.

Figure 3:
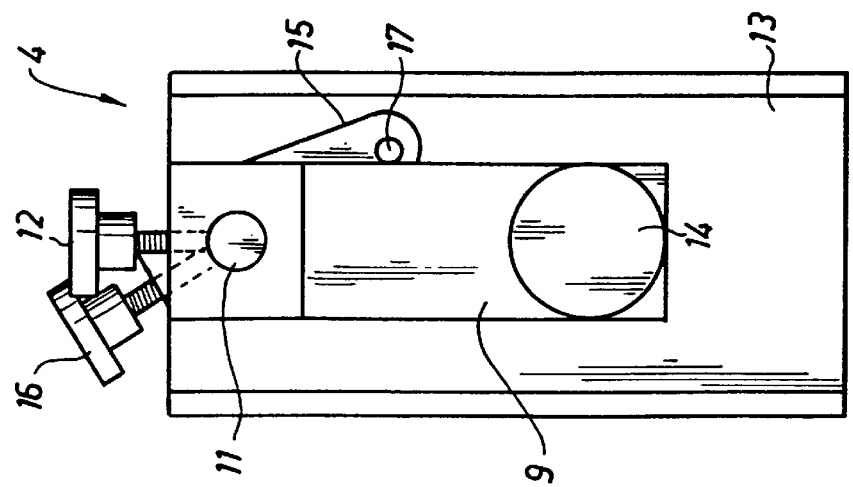
FIG. 3 is an end view of the device in FIG. 2.
Figure 2:
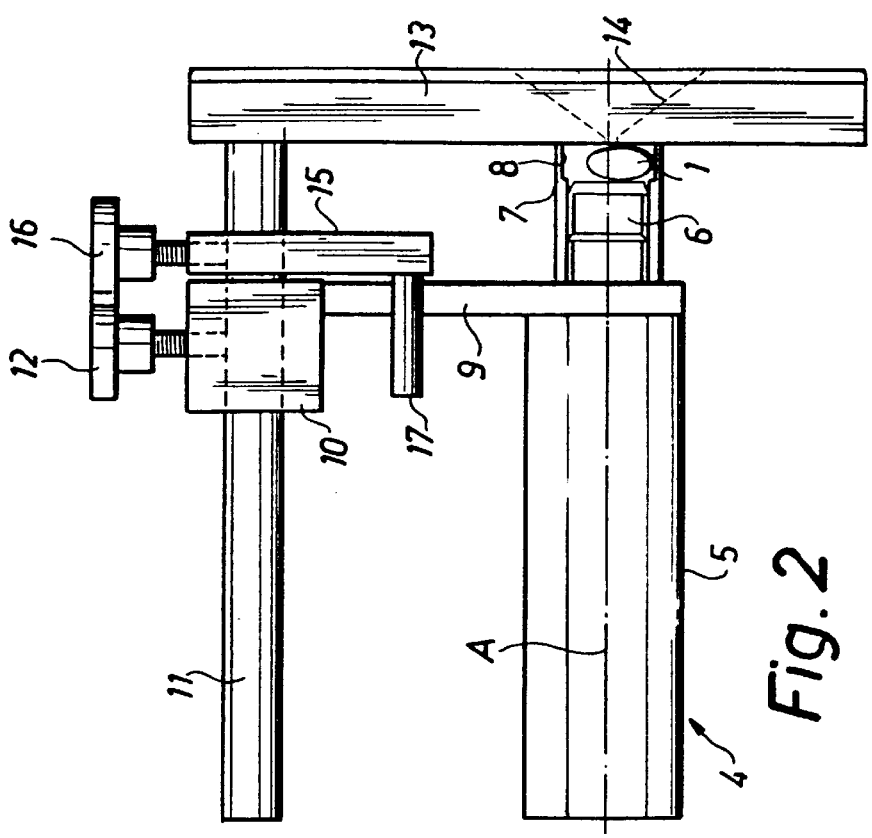
FIG. 2 is a side view of a device according to the first embodiment of the invention.

FIGS. 2 and 3 show a tablet holder of almost experimental construction, which is generally designated 4. The holder 4 comprises a motor 5, on whose horizontal output shaft 6 is mounted a cylinder 7 whose internal cylinder surface 8 defines a sample compartment for a tablet 1. The axis of rotation is designated A.

Figure 4B:
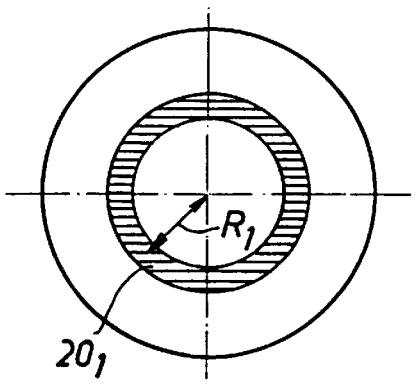
Figure 5B:
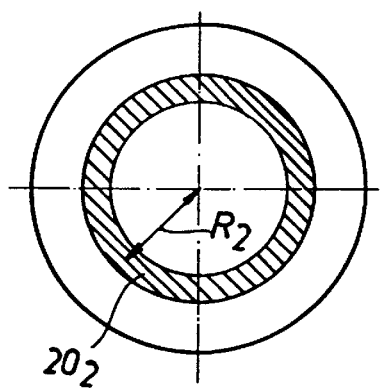
Figure 6A:
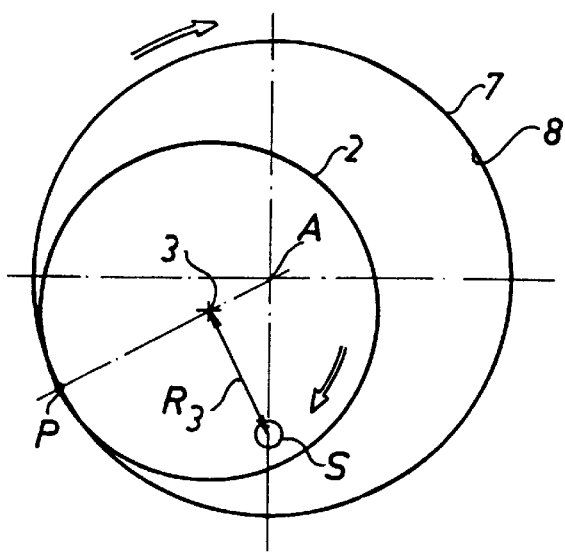
Figure 6B:
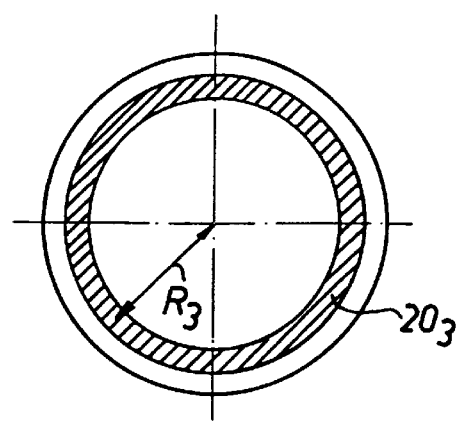

The diameter of the cylinder 7 is dimensioned according to the diameter of the tablet 1 and is especially, as shown in FIGS. 4–6, larger than the diameter of the tablet, such that the latter may perform the movement described below inside the sample compartment.

The motor 5 is supported at the lower end of an arm 9, whose upper end is mounted on a first attachment 10, which is adjustably mounted on a horizontal rod 11 which, in a manner not described in more detail here, is supported on a frame or the like. The first attachment 10 can be displaced along, as well as be angularly adjusted about, the rod 11 and be locked in the desired position with the aid of a first locking knob 12. The right-hand end (as seen in FIG. 3) of the rod 11 supports a rectangular baffle plate 13 extending vertically downwards and covering the open cylinder end facing away from the motor 5. The baffle plate 13 has a conical, circular and throughgoing radiation passage 14, whose narrow top opening opens into the sample compartment of the cylinder 7.

The holder 1 further comprises a second attachment 15, which also is so mounted on the rod 11 as to be displaceable and angularly adjustable as well as fixable in the desired position with the aid of a second locking knob 16. At the lower end, the second attachment 15 has an abutment 17 which projects in the direction of the arm 9 and which is intended to be applied against the motor-supporting arm 9 in order to define the angular position of the latter in relation to the rod 11.

When carrying out a Raman analysis of a tablet 1 with the aid of the tablet holder 4 shown in FIGS. 2 and 3, one first loosens the first attachment 10 and displaces the motor 5 with the associated cylinder 7 rearwards in relation to the baffle plate 13, so as to uncover the open end of the cylinder 7. Then, the sample (here the tablet 1) is placed in the sample compartment, as shown in FIG. 2. The first attachment 10 is returned to, and fixed in, its previous position shown in FIG. 2, and the axis of rotation A of the motor 5 may then, with the aid of the abutment 17 whose position is determined by the adjustment of the second attachment 15, be set in exactly the desired position in relation to the radiation passage 14, especially the same position for successive analyses of different samples.

A radiation source (not shown), such as a laser, is arranged on the opposite side of the baffle plate 13, and an excitation beam is focused on the reception surface of the tablet 1, as indicated by an impingement area S in FIGS. 4–6. The analysis is here carried out with the aid of back-scattering techniques, which means that radiation reflected by the tablet 1 exits through the conical passage 14 and is intercepted by a radiation detector (not shown), which is concentric with the excitation beam. The detected radiation is then in known manner converted to electric signals, which can be analysed with the aid of e.g. FT techniques.

Being well-known to those skilled in the art and not primarily forming part of this invention, the construction and the function of the radiation source, the radiation detector and the signal-processing electronics will not be described in any great detail here.

Figure 7:
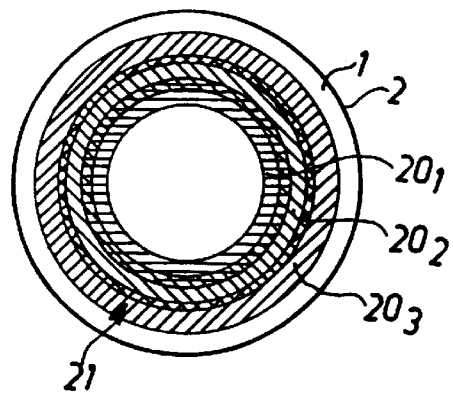

Reference is now made to FIGS. 4–7, which illustrate the principle on which works the tablet holder 4 in FIGS. 2 and 3. Owing to the rotation of the cylinder 7, the point of contact P between the circular peripheral surface 2 of the tablet 1 and the internal cylinder surface 8 of the cylinder 7 will move continuously along a circular arc from a first end position at approximately "six o'clock" (FIG. 4A) via an intermediate position (FIG. 5A) to a second end position at approximately "eight o'clock" (FIG. 6A). The distance between the point of impingement S of the excitation beam and the centre line 3 of the tablet in the different positions P is designated respectively $R_1$, $R_2$ and $R_3$. Since the tablet 1 rolls against the cylinder surface 8, the excitation beam will thus, for the three tablet positions shown, describe annular scanning traces $20_1$, $20_2$, $20_3$ having different-sized radii $R_1$, $R_2$ and $R_3$, respectively, according to FIGS. 4A–6A. Since P comes to occupy all the positions found between the end positions, the total surface 21 scanned will be a superposition of such annular scanning traces, i.e. a continuous annular surface 21 having a radial width much exceeding the diameter of the impingement area S of the excitation beam, as is schematically illustrated in FIG. 7.

FIG. 8 illustrates highly schematically the principle on which works a second embodiment of the invention. In order to alter the radius R of the scanning trace, the axis of rotation A of the sample (the tablet 1) is here displaced, continuously or stepwise during the implementation of the spectroscopic analysis, in relation to the excitation beam S. The means causing the displacement of the sample holder are not shown in FIGS. 8A–E, but the motor 5 with the associated cylinder 7 of the embodiment shown in FIGS. 2 and 3 may basically be mounted on a carrier, which can be displaced perpendicularly to the excitation beam, for instance vertically or horizontally, with the aid of some suitable drive means, such as a step motor.

In the Example illustrated, the symmetry line of the tablet 1 at all time coincides with the axis of rotation A, and the axis of rotation A is displaced in relation to the excitation beam. In FIG. 8A, the excitation beam coincides with the centre of rotation A, as is initially the case. Then, the sample holder, i.e. the axis of rotation A, is lowered stepwise, for instance in steps of approximately 2 mm, or is lowered continuously, such that the point of impingement S of the excitation beam becomes increasingly eccentric in relation to the axis of rotation A, thereby giving the scanned trace an increasing radius R. If the axis of rotation is continuously moved, the scanning trace will obtain a more spiral appearance. The total surface covered becomes a superposition of the successive part surfaces indicated in FIGS. 8A–E and can be made to cover essentially the whole radiation-receiving surface of the tablet 1.

The rotational speed of the inventive embodiments described above can be varied but may, for instance, be 10 rpm.

Further, it should be observed that, when need be, the sample may optionally be turned between different part analyses, thereby to achieve a more complete analysis of the whole volume of the sample.

We claim:

1. A device (4) for performing a spectroscopic analysis of a solid sample, said device (4) comprising a sample holder (7) for positioning the sample (1) in relation to an excitation beam which, during implementation of the analysis, falls upon a reception surface of the sample (1), the impingement area (S) being smaller than the reception surface of the sample (1), the device further comprising a drive means (5) for causing the sample holder (7) to rotate about an axis of rotation (A) parallel to the excitation beam, such that the point of impingement (S) of the excitation beam describes an annular scanning trace (20) on the reception surface of the sample (1), and means for optionally varying the radius (R) of the annular scanning trace (20) during implementation of the analysis.

2. A device (4) according to claim 1 for performing a spectroscopic analysis of a sample (1) having a circular peripheral surface (2), wherein the axis of rotation (A) of the holder (7) is non-vertical, preferably horizontal, and the sample holder (7) comprises a sample compartment defined by a cylinder surface (8) which is concentric with the axis of rotation (A) and rotates about it and whose diameter exceeds that of the circular peripheral surface (2) of the sample (1), the sample (1) being freely movable in the sample compartment and having its symmetry axis (3) directed in parallel with the axis of rotation (A) of the holder (7) so as to roll against the cylinder surface (8) when this rotates.

3. A device according to claim 2, wherein the sample compartment is so dimensioned that the sample (1) placed therein is essentially fixed in relation to the holder (7) in the direction of the axis of rotation (A) but is freely movable in relation to the holder (7) perpendicularly to the axis of rotation (A).

4. A device (4) according to claim 1, wherein said means for optionally varying the radius (R) of the annular scanning trace (20) arranged to parallel-displace the axis of rotation (A) of the holder (7) in relation to the excitation beam, thereby to achieve the variation of the radius (R) of the scanning trace (20).

5. A device according to claim 4, wherein the holder (7) keeps the sample (1) fixed in all directions in relation to the holder (7) during implementation of the analysis.

6. A method for performing a spectroscopic analysis of a solid sample, comprising the steps of generating an excitation beam and positioning the sample (1) by means of a sample holder (7) in relation to the excitation beam, such that the latter falls upon a reception surface of the sample (1), the impingement area (S) being smaller than the reception surface of the sample (1), the method further comprising the steps of rotating the sample holder (7) about an axis of rotation (A) parallel to the excitation beam, such that the point of impingement (S) of the excitation beam describes an annular scanning trace (20) on the reception surface of the sample (1), and varying the radius (R) of the annular scanning trace (20) during implementation of the analysis.

7. A method according to claim 6 for use in a spectroscopic analysis of a solid sample (1) having a circular peripheral surface (2), comprising the steps of arranging the axis of rotation (A) of the holder (7) in a non-vertical position, preferably a horizontal position, and placing the sample (1) on a cylinder surface (8) being concentric with and rotating about the axis of rotation (A) and having a diameter which exceeds that of the circular peripheral surface (2) of the sample (1), the sample (1) being so arranged that its symmetry axis (3) is parallel to the axis of rotation (A) of the holder (7), thereby to roll against the cylinder surface (8) when this rotates.

8. A method according to claim 7, comprising the step of fixing the sample (1) in relation to the holder (7) in the direction of the axis of rotation (A), but allowing the sample (1) to be freely movable in relation to the holder (7) perpendicularly to the axis of rotation (A).

9. A method in according to claim 6, comprising the step of parallel-displacing the axis of rotation (A) of the holder (7) in relation to the excitation beam, thereby to achieve the variation of the radius (R) of the scanning trace (20).

10. A method according to claim 9, comprising the step of keeping the sample (1) fixed in all directions in relation to the holder (7) during implementation of the analysis.

11. A method according to any one of claims 6–10, comprising the step of performing the spectroscopic analysis with the aid of Raman spectrometry.

12. A method according to claim 11, comprising the step of performing the spectroscopic analysis with the aid of back-scattering techniques.

* * * * *